United States Patent [19]

Ayers

[11] 4,373,263
[45] Feb. 15, 1983

[54] MOLDED IMPLANT REMOVAL KNIFE

[75] Inventor: Grover W. Ayers, Vinton, Va.

[73] Assignee: Eli Lilly and Company, Indianapolis, Ind.

[21] Appl. No.: 217,448

[22] Filed: Dec. 17, 1980

[51] Int. Cl.³ .............................................. B26B 29/00
[52] U.S. Cl. ........................................ 30/294; 30/333
[58] Field of Search ......................... 30/333, 332, 294

[56] References Cited

U.S. PATENT DOCUMENTS

| | | | |
|---|---|---|---|
| 880,765 | 3/1908 | Utter | 30/332 |
| 1,093,802 | 4/1914 | Richards | 30/333 |
| 1,359,722 | 11/1920 | Moffett | 30/333 |
| 1,518,100 | 12/1924 | Nighbert | 30/332 |
| 1,755,791 | 4/1930 | O'Neill | 30/333 |
| 1,791,855 | 2/1931 | Taylor | 30/333 |
| 1,957,663 | 5/1934 | Neidhart | 30/333 |
| 1,992,517 | 2/1935 | Watson | 30/333 |
| 2,291,294 | 7/1942 | Holste | 30/294 |
| 2,339,843 | 1/1944 | Dillon | 30/333 |
| 2,350,945 | 6/1944 | Treadway | 30/294 |
| 3,673,687 | 7/1972 | Phillips et al. | 30/294 |
| 3,824,688 | 7/1974 | Goffe | 30/294 |

FOREIGN PATENT DOCUMENTS 2720852  8/1978  Fed. Rep. of Germany ........ 30/294

Primary Examiner—Stephen G. Kunin
Assistant Examiner—J. T. Zatarga
Attorney, Agent, or Firm—Barnes & Thornburg

[57] ABSTRACT

Animal implantates may be removed by a knife that permits the insertion and removal of blades without the manipulation of fasteners. Such a knife may be inexpensively manufactured by molding two relatively simple pieces that can be fitted together to hold a scalpel blade and to permit its incision to be guided and limited in depth. One piece of such a knife forms a handle having a first portion adapted to be gripped by hand and a blade-carrying second portion forming two ribs with a central slot. The second piece is a blade carrier having a first side surface adapted to engage an opening in a blade to hold the blade in fixed position on the blade carrier. The blade carrier has an upper bearing surface adapted to engage a rib of the first handle portion and a surface projecting upwardly centrally of the bearing surface and being adapted to engage the ribs of the first portion. The blade carrier is assembled to the handle by inserting its upwardly projecting portion into the central slot of the handle where it is fixedly retained. When assembled, the two pieces hold the blade in position for use.

3 Claims, 10 Drawing Figures

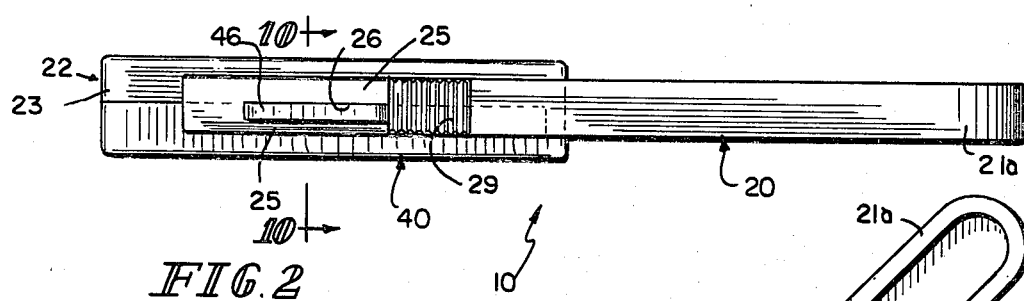
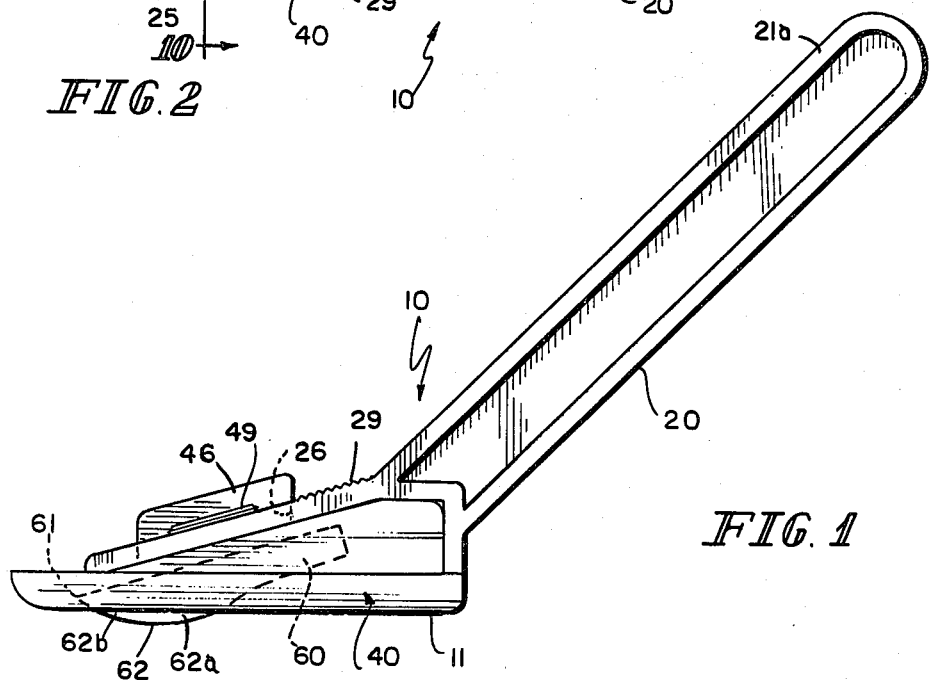
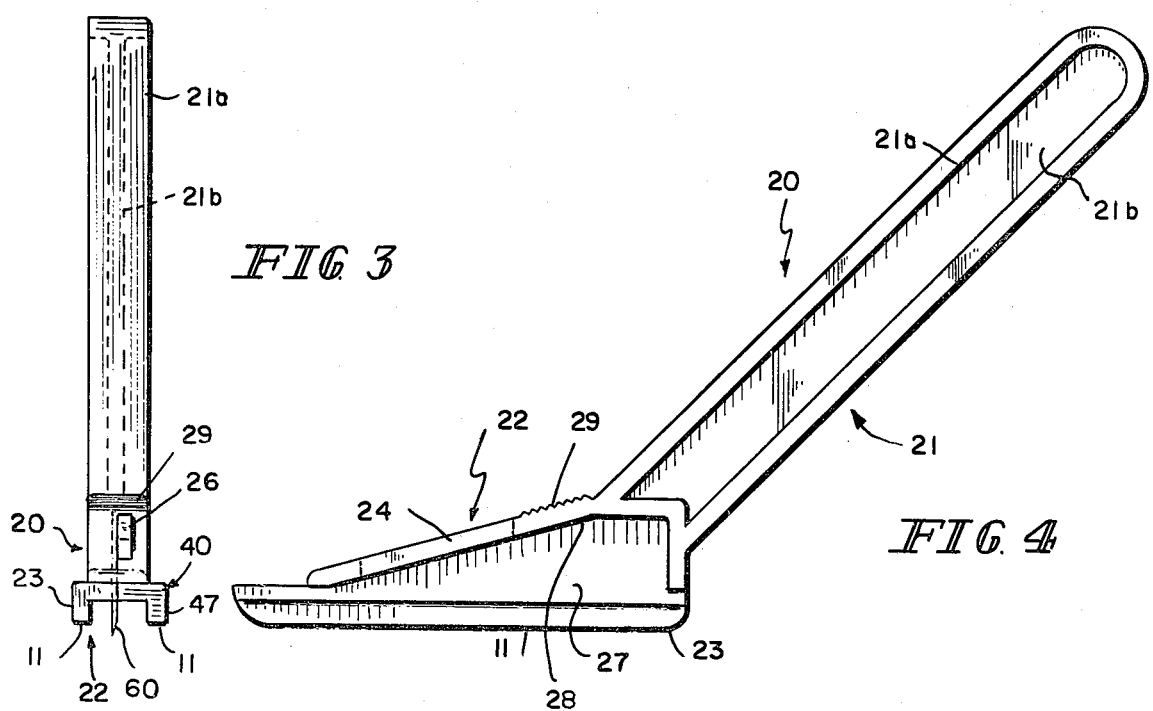

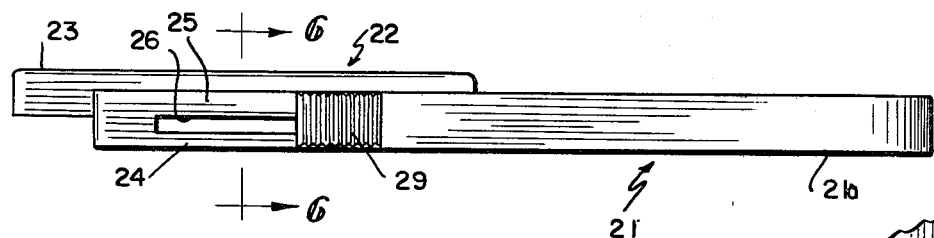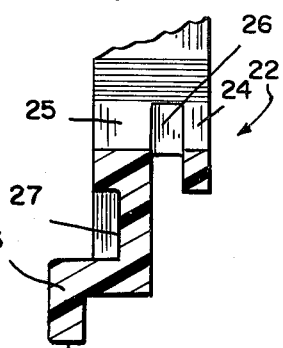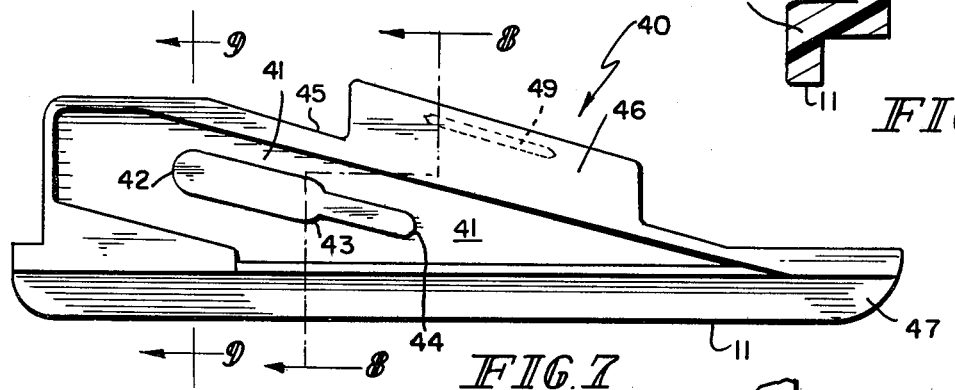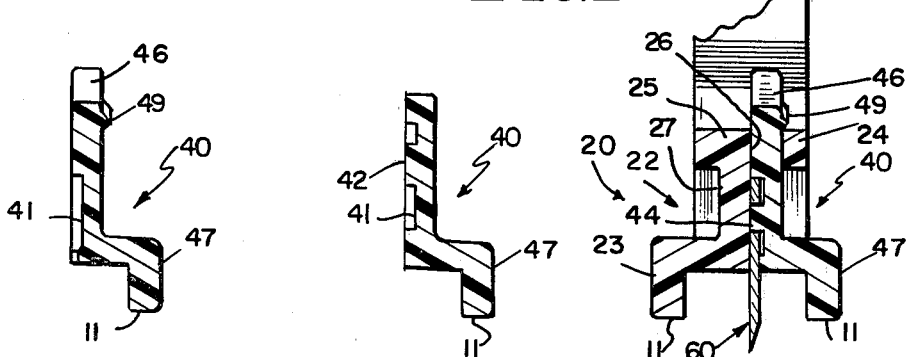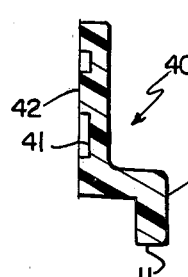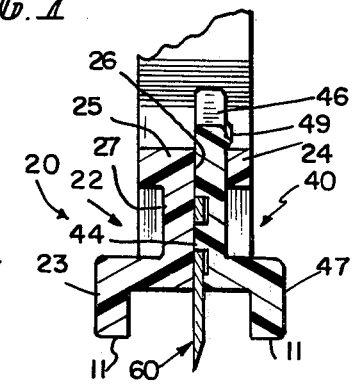

MOLDED IMPLANT REMOVAL KNIFE

This invention relates to an inexpensive and disposable implant removal knife and more particularly to a molded, two-piece handle that can hold a scalpel blade for use in removing subcutaneous implants from the body of an animal and that permits the insertion and removal of the scalpel blade without fasteners.

Growth stimulants, such as diethylstilbesterol, have been introduced as small pellets into the ears of livestock, such as cattle, to increase the rate of weight gain and to improve feed conversion. Diethylstilbesterol is a powerful hormone-like substance, and the quantity introduced into each animal is small. The pellets implanted in each animal have been correspondingly small and are gradually carried away by the animal's body fluids. After introduction of such implants into an animal, periods of several months or more are required for dissipation of the drug from the body of the animal prior to its slaughter. In addition, the ears or the portion of the animal into which the substance is implanted must be thrown away.

More recently, implantates have been developed to introduce therapeutic agents into the body of an animal by providing a uniform release of the drugs over long periods of time. Such implantates are not eroded by the animal's body fluids and permit the exposure of the animal to the effect of the drug to be terminated at will by removal of the implantate.

With termination of exposure of the body of the animal to the effect of the drug thus controllable, the livestock owner has the ability to more rapidly meet the demands of the marketplace by electing to shorten the time between treatment of the animal with a drug, such as a growth stimulant, and slaughtering of the animal for use.

Such removable implantates comprise a drug carrier formed of an organopolysiloxane rubber composition (more generally known as silicone rubber) which is nonreactive toward the drug, nontoxic to the body, and known to be compatible with living tissue even after prolonged implantation. The drugs are in powder or semisolid or liquid form, and generally have an appreciable solubility in the polymer composition of the organopolysiloxane rubber composition. Such drugs are introduced from the carrier into the body of the animal by diffusion or migration interstitially between the elastomer molecules to the outer surface of the carrier from which they are removed by the animal's body fluids. The term "drug" is used in its broad sense as synonymous with therapeutic agent, medicament, and the like, and is intended to include hormones, vitamins, antibiotics, anticoagulants, cancericidal agents, spermicidal agents, vasoactive agents, and other medicinals and medications effective to treat undesirable conditions existing in or on an animal body or in the animal's body fluids.

An implant removal knife that permits the removal of such an implantate from under the skin of an animal, upon completion of its treatment, is known. Such a knife includes a handle and a blade-receiving portion projecting at an obtuse angle from the handle and providing a surface for the application of pressure from the thumb of the hand that grips the handle to concentrate severing and cutting force on the edge of the blade. The knife was adapted to employ a surgical scalpel blade having a curved cutting edge and to use an aperture of the blade to hold the blade securely in the blade-receiving portion.

The known knife was formed with two principal means. The first means formed the handle and part of the blade-receiving portion. The remainder of the blade-receiving portion of the knife was a separate second means fastened to the first handle-forming means by screws in such manner that it was pivoted to permit insertion and removal of the blade. The central inner faces of the portion of the knife that received the blade included surfaces shaped to engage and position the blade. The aperture of the scalpel blade engaged a mating projecting surface and corresponding depression in the central inner faces, permitting the blade to be positioned centrally within the blade-receiving portion. The curved cutting edge of the scalpel blade projected from the blade-receiving portion only a fraction of an inch with the cutting edge forming acute angles with respect to the blade-receiving portion where it projected. The end of the scalpel blade was held concealed within the blade-receiving portion so that its pointed end was not exposed.

The blade-receiving portion of the knife included two blade-guiding surfaces parallel with the plane of the cutting edge of the blade, permitting the user to locate and guide the incision by which a subcutaneous implant was exposed for removal. One of the guiding surfaces was formed in each of the two principal means that comprised the knife, and the guiding surfaces formed a channel on the underside of the blade-receiving portion with the blade projecting within the channel, thus permitting control of the depth and direction of any incision made. The cutting edge of the blade was located with respect to a subcutaneous implant by positioning the channel over the implant.

The known knife was effective for both severing and slicing action and permitted the use of the thumb of the hand to concentrate force on the edge of the blade to provide the pressure needed to open the body of an animal. The blade-receiving portion of the knife included guiding surfaces to permit both control of the depth of the incision and location of the incision along the longitudinal axis of a subcutaneous implant.

The known knife, however, was bulky and expensive. Because implant removal knives are used in the field and remote from any sterilizing facility, it is frequently necessary that many such knives be used in actual practice to avoid infection of the animals. The cost of such knives is, therefore, a significant consideration in the use of the implantate system of growth stimulation.

The use of fasteners was also disadvantageous. The surfaces of fasteners have deep recesses and sites that are difficult to clean, and fasteners can provide sites of contamination that may lead to the infection of the animals on which such knives are used. Furthermore, the manipulation of fasteners is difficult in the field; corrosion and the inability to loosen the fasteners because of contamination frequently become problems in the field.

This invention is therefore directed to an inexpensive implant removal knife providing the advantages of the known knife and comprising only two simple, easily assembled, and easily cleansed parts. The knife of this invention may be manufactured by molding, consist of a small quantity of material, and yet provide transmission and control of cutting force to a blade edge. The knife is adapted to provide insertion and placement of a scalpel blade by simple assembly of one part to another and without manipulation of fasteners. One piece of the knife is adapted to engage and carry the blade and to be fitted into another handle-forming piece.

The invention includes, as one piece, a handle having a first portion adapted to be gripped by hand and an integral second portion forming two ribs with a central slot. The second piece is a blade carrier having a first side surface adapted to engage an opening in a blade, such as a scalpel blade, and to hold the blade in fixed position on the blade carrier. The blade carrier has an upper handle-engaging surface with a bearing surface adapted to engage the ribs of the second handle portion and a frictional or a snap-fitting surface projecting upwardly and centrally of its bearing surface and adapted to engage fixedly the ribs of the second handle portion. The two pieces, when assembled, hold and position the blade between them for use and permit it to be inserted and removed without the manipulation of fasteners.

In a preferred embodiment, the ribs are resilient in a direction transverse to the central plane of the knife to permit a snap-fitting surface to carry a snap rim through the slot but are sufficiently rigid in the direction of the central plane of the knife to transmit force from the handle to the blade.

Thus, this invention provides a molded scalpel-blade holder comprising a handle with a blade-carrying portion extending from the handle, and preferably forming an obtuse angle with the handle. The blade-carrying portion of the handle has a ribbed upper portion and can be provided with a downwardly extending flange integrally connected with the handle. The ribber upper portion extends on either side of a slot in the blade-carrying portion of the handle. A blade carrier is adapted to engage the scalpel blade on one side, can be shaped with its other side surface forming a second downwardly extending flange, and can have an upwardly extending portion adapted to fit and be fixedly retained within the slot of the blade-carrying portion of the handle.

Implant removal knives of this invention can be made inexpensively, can comprise two easily assembled pieces to position and hold a scalpel blade for use, can eliminate fasteners and the contamination and difficult manipulation associated with fasteners, and can provide a knife which is easily cleaned and sterilized or may be discarded.

Other features and advantages of the invention will be apparent from the following drawings and descriptions in which:

FIG. 1 is a side elevational view of an assembled knife of this invention, showing the manner in which it supports a blade in phantom lines;

FIG. 2 is a top view of the knife of FIG. 1;

FIG. 3 is a front elevational view of the knife of FIG. 1;

FIG. 4 is a side elevational view of the handle-forming portion of the knife with the blade-carrying member removed;

FIG. 5 is a top view of the handle-forming portion of FIG. 4;

FIG. 6 is a cross-sectional view of the blade-carrying portion of the handle-forming member taken along line 6—6 of FIG. 5.

FIG. 7 is a side elevational view of the blade-carrying member of the knife showing its inner face;

FIG. 8 is a cross-sectional view of the blade-carrying member of the knife taken along line 8—8 of FIG. 7;

FIG. 9 is a cross-sectional view of the blade-carrying member of FIG. 7 taken along line 9—9 of FIG. 7; and FIG. 10 is a cross-sectional view of the blade-carrying portion of the assembled knife including a blade, and taken along line 10—10 of FIG. 2.

As illustrated in the drawings, a knife 10 of this invention includes two pieces: a handle-forming piece 20 and a blade-carrying piece 40. The two pieces, upon assembly, as shown in FIG. 1, may support a scalpel blade 60 in such a manner that its pointed end 61 is not exposed but is protected within the knife, and in such a manner that the cutting edge 62 of the scalpel blade projects from the knife only a small fraction of an inch and forms, with the lowermost surfaces 11 of the knife, a pair of acute angles 62a and 62b. As may be seen in FIG. 1 and FIG. 3, the pieces, when assembled, form a pair of downwardly depending flanges 23 and 47 and lowermost surfaces 11 that are parallel and equally spaced on either side of the blade to limit exposure of the blade and the depth of the incision that may be made with the knife and to provide a pair of surfaces that may be used to guide the blade edge 62 in making an incision along the elongated axis of an implantate.

The first piece 20 which forms the knife handle and carries the blade can best be seen in FIGS. 4-6.

The first, or handle-forming, portion 21 of the first piece 20 can be about four and one-half inches in length from its distal end to the point at which it extends into the blade-carrying portion 22 and can have a width along its central plane of between five-eighths to three-quarters of an inch. The handle portion 21 is provided with a continual peripheral rib 21a on both sides of its central plane to provide total handle thickness of about three-eighths of an inch at the periphery. The rib extends in the direction of the central plane of the knife approximately one-tenth of an inch. The handle portion also includes a central web 21b situated on the central plane of the knife and having a thickness of approximately one-tenth of an inch. The handle portion 21 of the knife thus provides substantial rigidity with a minimum of material.

The second, or blade-carrying portion, 22 of the first piece 20 extends from the handle-forming portion 21 to define generally an included obtuse angle, as shown in FIG. 4. The blade-carrying portion 22 includes a downwardly depending flange 23 that forms one of the lowermost surfaces 11 of the knife. As shown in FIG. 4, the lowermost portion 11 of the first piece 20 lies in a substantially straight line whose extension forms an included acute angle of about 45° with respect to the axis of handle portion 21. The blade-carrying portion 22 of the first piece 20 also includes, as its uppermost surface, ribs 24 and 25 (FIG. 5) that are integrally formed with handle-forming portion 21 and that define a central slot 26 in the blade-carrying portion 22 of the first piece 20. As best seen in FIGS. 5 and 6, the central slot 26 is centrally located between the ribs 24 and 25 but, as shown in this preferred embodiment, is located off-center from the central plane of the knife. Thus, rib 24, which lies on the side of the central plane of the knife that receives the blade-carrier second piece 40 (see FIG. 10), is thinner than rib 25 which is integrally connected with the central web 27 of the blade-carrying portion 22 of the first piece 20. This arrangement of the preferred embodiment permits sufficient flexibility in rib 24 to permit the insertion of the second piece 40 into the first piece 20.

The blade-carrying portion 22 of the first piece 20 also defines an interior surface 28, as shown in FIG. 4, against which the second piece 40 may bear. Immediately above surface 28, the blade-carrying portion 22 of the first piece is provided with a serrated surface 29 to permit pressure to be conveniently transmitted from the hand of the user to the blade 60. The uppermost surface of the blade-carrying portion 22, including ribs 24 and 25 and the serrated surface 29, extends downwardly from the handle portion 21 in such a manner that a line parallel with its upper surface will form an included angle of about 15° with respect to a line in which the lowermost surface 11 lies. The downwardly depending flange 23 and the central web 27 each have a thickness of about one-tenth of an inch. The thickness of the upper surface of the blade-carrying portion 22 including ribs 24 and 25 is equal to the thickness of the ribs 21a of the handle-forming portion 21, or about three-eighths of an inch. The downwardly depending flange 23 of the blade-carrying portion has a length of about three inches from the point where it joins handle portion 21 to its forwardmost extremity.

The preferred embodiment of the second piece, or blade carrier, 40 is shown in FIGS. 7–9. As shown in FIGS. 7 and 9, the inside surface 41 of the second piece 40 may be provided with a raised boss having portion 42, 43, and 44 shaped to fit and to carry the blade 60. The inside surface 41 of the blade carrier 40 can thus be adapted to engage the holes provided in a standard scalpel blade and to maintain the blade in fixed position with respect to the blade carrier 40. The uppermost surface of blade carrier 40 is provided with a portion 45 adapted to engage, upon assembly to the first piece 20, its interior surface 28 (FIG. 4) and an upward projection 46 adapted to fit slot 26 of the blade-carrying portion 22 of the first piece 20. The blade carrier 40 also includes a downwardly depending flange 47 defining, upon assembly into the knife 10, one of the lowermost surfaces 11. A line parallel with the bearing surface 45 thus forms an included angle of 15° with respect to the line on which lowermost surface 11 of the blade carrier 40 lies. The innermost surface 41 is contoured to engage the sides of scalpel blade 60. The blade-engaging bosses 42, 43, and 44 project outwardly from the innermost surface 41 approximately 0.035 of an inch. The upwardly extending slot-engaging surface of the blade-carrying member has a thickness of about 0.085 of an inch and may be provided with a snap rib 49 projecting outwardly from the surface at a location above rib 24 when the second piece 40 is assembled to the first piece 20 (see FIG. 1). In this regard, the width of the central slot 26 formed in the first piece 20 is preferably 0.085 of an inch plus draft so that preferably the projection 46 of the second piece 40 has line-to-line contact with the ribs 24 and 25 of the first piece 20 upon assembly. The downwardly depending flange 47, like flange 23, has a length of three inches and is positioned with respect to the upwardly extending slot-engaging surface 46 so that, upon assembly of the second piece 40 with the first piece 20, it matches the downwardly depending flange 23 of the first piece as shown in FIGS. 2, 3, and 10.

Upon assembly of the knife, a scalpel blade 60 is positioned on the blade-carrying second piece 40 on the boss, 42, 43, and 44. Blade carrier 40 is fitted to the first handle-forming piece 20 by placing its upwardly depending surface 46 within slot 26 and pushing blade carrier 40 upwardly until its upper surface 45 engages the inner surface 28 of the first piece 20. As shown in FIGS. 1 and 10, the upwardly projecting surface 46 extends beyond ribs 24 and 25. The second piece 40 may be fixedly retained by the first piece 20 through frictional engagement or "snap-fitting" engagement. Preferably, upwardly projecting surface 46 can be provided with a snap rib 49 and rib 24 can be sufficiently resilient to permit the passage of the snap rib 49 through slot 26 to enhance the fixed retention of second piece 40 by the first piece 20. The length of such a snap rib 49 is preferably about 7/16 of an inch long and its projection from the second piece 40 preferably lies in the range of 0.020 to 0.030 of an inch. As shown in FIG. 10, upon assembly, the second piece 40 is held within the slot 26 by ribs 24 and 25 in such a manner that blade 60 is trapped between the two pieces that form the knife; and as so assembled, the blade 60 is held in position between downwardly depending flanges 23 and 47 and the lowermost surfaces 11 of the knife. When a change of blades is needed or desired, the knife 10 may be easily disassembled by the user pressing downwardly upon the uppermost surface 46 of the second piece, thus pressing the second piece 40 from its engagement with the first piece 20 of the knife 10 and permitting the scalpel blade to be removed from the second piece.

As illustrated, a knife of this invention may be formed with two pieces having generally uniform thickness of a character which permits it to be easily molded with a minimum of material and yet provides sufficiently structural rigidity and integrity that it may be used to securely carry and provide controllable incisions with a scalpel blade. The knife may be easily assembled and disassembled without the use and manipulation of fasteners. The surfaces of the knife are smooth and simply shaped with a minimum of complicated recesses that are difficult to clean and may form sites of contamination and infection. Because of the small size, light weight, and inexpensive character of the knife of this invention, a number of such knives may be inexpensively put to use in the field and, if necessary, may be treated as expendable.

Although the knife of this invention may be molded from any one of a number of thermoplastic molding materials, it is preferably molded from ABS (Acrylonitrile-butadiene-styrene copolymers) and provided with a fine matt finish. As is known by those skilled in the art, the part can be provided with such radii and draft, as are convenient in molding parts of such size and shape. Generally the drafts provided may be on the order of 2° and fillets and radii on the order of 0.010 to 0.015 of an inch.

Although a particularly preferred embodiment has been shown and described, the scope of this invention is set forth in the claims that follow.

What is claimed is:

1. An implant removal knife including two pieces adapted for manufacture by molding and for assembly without fasteners, comprising
    a molded unitary first piece forming a handle portion and an integral blade-carrying portion extending forwardly from the handle portion at an obtuse angle, said handle portion and blade-carrying portion including a central web and a pair of ribs, said pair of ribs extending outwardly on each side of the central web at the periphery of the handle portion and extending forwardly at an obtuse angle to form an upper planar surface over the blade-carrying portion, one of the ribs at one side of the central web portion of the blade-carrying portion having a central slot to provide a resilient rib portion, said blade-carrying portion further including a flange depending downwardly from the planar surface and forming a straight lower edge intersecting the axis of the handle at an acute angle, and a molded second piece engaging the blade when assembled to the first piece, said second piece including an upwardly projecting surface having a thickness about equal to the width of the central slot in the blade-carrying portion of the first piece and having a snap rib, an interior surface shaped to engage the blade and a flange depending downwardly and parallel to the interior surface and forming a straight lower edge, said second piece being assembled to said first piece with upwardly extending surface of the second piece inserted into the central slot of the first piece, said snap rib having passed the resilient rib portion of the first piece so that the resilient rib portion retains the second piece to the first piece with the snap rib above the planar surface and so that the lower edge of the downwardly depending flange of the second piece is parallel to the lower edge of the downwardly depending flange of the first piece and so that said lower edges form a pair of parallel edges spaced outwardly from the central web of the blade-carrying portion and interior surface of the second piece, and whereby upon assembly a blade may be retained between said two pieces and held at an obtuse angle with respect to said handle and at an acute angle with respect to the spaced lower edges of the downwardly depending flanges of the first and second pieces.

2. An implant removal knife including two pieces adapted for manufacture by molding and for assembly without fasteners, comprising a molded unitary first piece forming a handle portion and an integral blade-carrying portion extending forwardly from the handle portion at an obtuse angle, said handle portion and blade-carrying portion including a central web and a pair of ribs, said pair of ribs extending outwardly on each side of the central web at the periphery of the handle portion and extending forwardly into the blade-carrying portion and forming an upper planar surface of the blade-carrying portion and inner surfaces partially surrounding the blade-carrying portion, one of the ribs at one side of the central web portion of the blade-carrying portion having a central slot to provide a resilient rib portion and forming one of the inner surfaces, partially surrounding the blade-carrying portion, and a molded second piece engaging the blade when assembled to the first piece, said second piece including an upper portion shaped to mate the partially surrounding inner surface of the blade-carrying portion and of the first piece, a surface projecting upwardly from the upper portion with a thickness and shape to engage the central slot in the blade-carrying portion of the first piece and an interior surface shaped to engage the blade, said second piece being assembled to said first piece with upwardly extending surface of the second piece inserted in the central slot of the first piece and engaged by the resilient rib portion of the first piece so that the resilient rib portion retains the second piece to the first piece with the upper portion of the second piece in contact with the one partially surrounding inner surface of the blade-carrying portion of the first piece, and whereby upon assembly a blade may be held between said two pieces with the partially surrounding inner surface of the blade-carrying portion of the first piece transmitting force to the assembled second piece and the blade.

3. An implant removal knife including two pieces adapted for manufacture by molding and for assembly without fasteners, comprising a molded unitary first piece forming a handle portion and an integral blade-carrying portion extending forwardly from the handle portion at an obtuse angle, said handle portion and blade-carrying portion including a central web and a pair of ribs, said pair of ribs extending outwardly on each side of the central web at the periphery of the handle portion and extending forwardly at an obtuse angle and forming an upper planar surface of the blade-carrying portion and inner surface partially surrounding the blade-carrying portion, one of the ribs at one side of the central web portion of the blade-carrying portion having a central slot to provide a resilient rib portion, said blade-carrying portion further including a flange depending downwardly from the planar surface and forming a straight lower edge intersecting the axis of the handle at an acute angle, and a molded second piece engaging the blade when assembled to the first piece, said second piece including an upper portion shaped to mate the one partially surrounding inner surface of the blade-carrying portion of the first piece, an upwardly projecting surface having a thickness about equal to the width of the central slot in the blade-carrying portion of the first piece and having a snap rib, an interior surface shaped to engage the blade, and a flange depending downwardly and parallel to the interior surface and forming a straight lower edge, said second piece being assembled to said first piece with upwardly extending surface of the second piece inserted into the central slot of the first piece, said snap rib having passed the resilient rib portion of the first piece so that the resilient rib portion retains the second piece to the first piece with the snap rib above the planar surface and with the upper portion of the second piece mating the one partially surrounding inner surface of the blade-carrying portion of the first piece and so that the lower edge of the downwardly depending flange of the second piece is parallel to the lower edge of the downwardly depending flange of the first piece and so that said lower edges form a pair of parallel edges spaced outwardly from the central web of the blade-carrying portion and interior surface of the second piece, and whereby upon assembly a blade may be held between said two pieces and engaged by the central web of the first piece and the interior surface of the second piece and held at an obtuse angle with respect to said handle and at an acute angle with respect to the spaced lower edges of the downwardly depending flanges of the first and second pieces.

* * * * *